(12) United States Patent
Levin et al.

(10) Patent No.: US 8,901,489 B2
(45) Date of Patent: Dec. 2, 2014

(54) LOOPED IONIZATION SOURCE

(75) Inventors: Daniel Levin, Laval (CA); Vlad Sergeyev, Laval (CA); Volodimir Bondarenko, Laval (CA); Bohdan Atamanchuk, Laval (CA); Qunzhou Bian, Laval (CA); Henryk Zaleski, Laval (CA); Mark Piniarski, Laval (CA); Simon Feldberg, Laval (CA); Ronald Jackson, Laval (CA)

(73) Assignee: Smiths Detection Montreal Inc., Montreal (CA)

( * ) Notice: Subject to any disclaimer, the term of this patent is extended or adjusted under 35 U.S.C. 154(b) by 0 days.

(21) Appl. No.: 14/126,259

(22) PCT Filed: Jun. 15, 2012

(86) PCT No.: PCT/IB2012/001669
§ 371 (c)(1),
(2), (4) Date: May 15, 2014

(87) PCT Pub. No.: WO2012/172436
PCT Pub. Date: Dec. 20, 2012

(65) Prior Publication Data
US 2014/0246581 A1  Sep. 4, 2014

Related U.S. Application Data

(60) Provisional application No. 61/497,681, filed on Jun. 16, 2011.

(51) Int. Cl.
*H01J 49/00* (2006.01)
*G01N 27/62* (2006.01)
*H01J 49/12* (2006.01)

(52) U.S. Cl.
CPC .............. *G01N 27/622* (2013.01); *H01J 49/12* (2013.01)
USPC ........... 250/288; 250/281; 250/282; 250/283; 250/287; 250/289; 250/290; 250/291; 250/292

(58) Field of Classification Search
USPC .................... 250/281–283, 287–292
See application file for complete search history.

(56) References Cited

U.S. PATENT DOCUMENTS 5,420,424 A * 5/1995 Carnahan et al. ............. 250/287
2002/0162967 A1* 11/2002 Atkinson et al. ............. 250/425
2008/0272285 A1* 11/2008 Giannantonio et al. ...... 250/281

* cited by examiner

*Primary Examiner* — Jack Berman
*Assistant Examiner* — Meenakshi Sahu
(74) *Attorney, Agent, or Firm* — Casimir Jones S.C.

(57) ABSTRACT

Looped ionization sources for ion mobility spectrometers are described. The ionization sources can be used to ionize molecules from a sample of interest in order to identify the molecules based on the ions. In an implementation, an electrical ionization source includes a wire that is looped between electrical contacts. The wire is used to form a corona responsive to application of voltage between the wire and the walls of an ionization chamber. The corona can form when a sufficient voltage is applied between the wire and the walls. A difference in electrical potential between the wire and a wall forming an ionization chamber, in which wire is contained, can be used to draw the ions away from the wire. In embodiments, the wire can be heated to reduce the voltage used to strike the corona. The ions, subsequently, may ionize the molecules from the sample of interest. The looped corona source can also be used in mass spectrometers (MS).

18 Claims, 6 Drawing Sheets

LOOPED IONIZATION SOURCE

CROSS-REFERENCE TO RELATED INFORMATION

The present invention claims the benefit of U.S. Provisional Application Ser. No. 61/497,681, filed Jun. 16, 2011, which is incorporated by reference in its entirety.

FIELD OF THE INVENTION

The present disclosure relates to looped ionization sources that can be used in, for example, ion mobility spectrometers or mass spectrometers. In certain embodiments, the looped ionization sources are used to ionize molecules from a sample of interest in order to identify the molecules based on the ions. In particular embodiments, an electrical ionization source includes a wire that is looped between electrical contacts that is used to form a corona responsive to application of voltage between the wire and the walls of an ionization chamber.

BACKGROUND

Ion mobility spectrometers (IMS) use an ionization source to ionize molecules from a sample of interest to identify the molecules. Once the molecules are ionized, the IMS measures the time it takes the ions to reach a detector. This type of IMS is referred to as a time-of-flight IMS. The IMS can use the ion's time-of-flight to identify the molecule because different ions have different time-of-flights based on the ion's ion mobility.

An IMS can include a radioactive source or an electrical source to ionize the molecules. For example, an IMS may include a radioactive nickel 63 ($^{63}$Ni) source to ionize molecules. IMSs with electrical sources ionize molecules by discharging an electrical current. While different voltages can be used, an electrical source's voltage typically is sufficiently high to cause the molecule to have a single positive or negative charge, although fragmentation and different mass to charges ratios are possible.

SUMMARY

Looped ionization sources useful in, for example, ion mobility spectrometers or other devices are described. The ionization sources can be used to ionize molecules from a sample of interest in order to identify the molecules based on the ions. In an implementation, an electrical ionization source includes a wire that is looped between electrical contacts. The wire is used to form a corona responsive to application of voltage between the wire and the walls of an ionization chamber. The corona can form when a sufficient voltage is applied between the wire and the walls. A difference in electrical potential between the wire and a wall forming an ionization chamber, in which wire is contained, can be used to draw the ions away from the wire. In embodiments, the wire can be heated to reduce the voltage used to strike the corona. The ions, subsequently, may ionize the molecules from the sample of interest.

In some embodiments, the present disclosure provides spectrometers comprising: a) a wall, that is capable of conducting electricity, that forms an ionization chamber; and b) an ionization source, that is looped, disposed in the ionization chamber, the ionization source being configured to conduct electrical current between electrical connections and exhibit a potential differential between the ionization source and the wall to form a corona.

In certain embodiments, the spectrometer comprises an ion mobility spectrometer configured to operate substantially at ambient pressure. In other embodiments, the ionization source comprises a looped wire configured to strike a corona substantially adjacent to the looped wire's midpoint. In particular embodiments, the ionization source is configured to strike a corona at approximately one thousand degrees Celsius (e.g., 950° C. . . . 1000° C. . . . 1100° C.). In further embodiments, the ionization source comprises a wire formed of at least one of: platinum; rhodium; nichrome; iridium; tungsten; tantalum; a platinum-rhodium alloy; a platinum-rhodium-irridium alloy; a platinum-irridium alloy; or an iron-chromium-aluminum alloy. In other embodiments, the wire is configured to pass electricity from one of the electrical connections to another of the electrical connections. In some embodiments, the ionization source is configured to strike a corona at approximately the ionization source's orange hot temperature. In additional embodiments, the current comprises an alternating electrical current or a direct electrical current. In certain embodiments, the wire is formed as a coil.

The present disclosure provides ion mobility spectrometers, comprising: an ionization source comprising: a looped wire that is electrically conductive and that extends between two electrical connections that are electrically insulated from a wall of an ionization chamber that contains the ionization source, wherein the ionization source and the wall are configured to be charged to different electrical potentials, so ions formed adjacent to the looped wire are drawn towards the wall.

In certain embodiments, the ionization source is configured to pass an alternating electrical current through the looped wire. In some embodiments, the looped wire's diameter is between twenty and eighty micrometers (20-80 μm) (e.g., 20 . . . 30 . . . 45 . . . 55 . . . 70 . . . and 80). In some embodiments, the looped wire is coiled or rounded along the wire's length. In additional embodiments, the ionization chamber is substantially at ambient pressure. In certain embodiments, the looped wire is formed of at least one of: platinum; rhodium; nichrome; iridium; tungsten; tantalum; a platinum-rhodium alloy; a platinum-rhodium-irridium alloy; a platinum-irridium alloy; or an iron-chromium-aluminum alloy. In particular embodiments, the ionization source is configured to form a corona generally about the looped wire's mid-point along the looped wire's length.

The present disclosure provides ion mobility spectrometer, comprising: a wall, formed of an electrically conductive material, that defines an ionization chamber; and a wire that is looped between electrical contacts that are electrically insulated from the wall, the wire being configured to form a corona along the wire's length to ionize a molecule, from a sample of interest, wherein the wall is configured to carry an electrical charge to draw ions from the corona towards the molecule.

In some embodiments, the wire is configured to be hotter along the wire's midpoint than at the wire's ends adjacent to the electrical contacts. In additional embodiments, the wire's diameter is between twenty and eighty micrometers (20-80 μm) and the wire's length is between one to one hundred millimeters (1-100 mm) long. In further embodiments, the ion mobility spectrometer is configured to apply an electrical current of approximately 0.7 amps on the wire to cause the corona. In particular embodiments, the wire is configured to form the corona at approximately one thousand degrees Celsius (1000° C.). In additional embodiments, the ion mobility spectrometer is configured to pass at least one of an alternating current or a direct current through the wire to heat the wire.

The present disclosure provides spectrometers comprising: an ionization chamber; and an ionization source, disposed in the ionization chamber, wherein the ionization source is a loop and wherein the ionization source can conduct electrical current and wherein a potential differential can be formed between the ionization source and a wall to form a corona.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. In the figures, the left-most digit(s) of a reference number identify the figure in which the reference number first appears. The use of the same reference number in different instances in the description and the figures may indicate similar or identical items.

DETAILED DESCRIPTION

Figure 1:
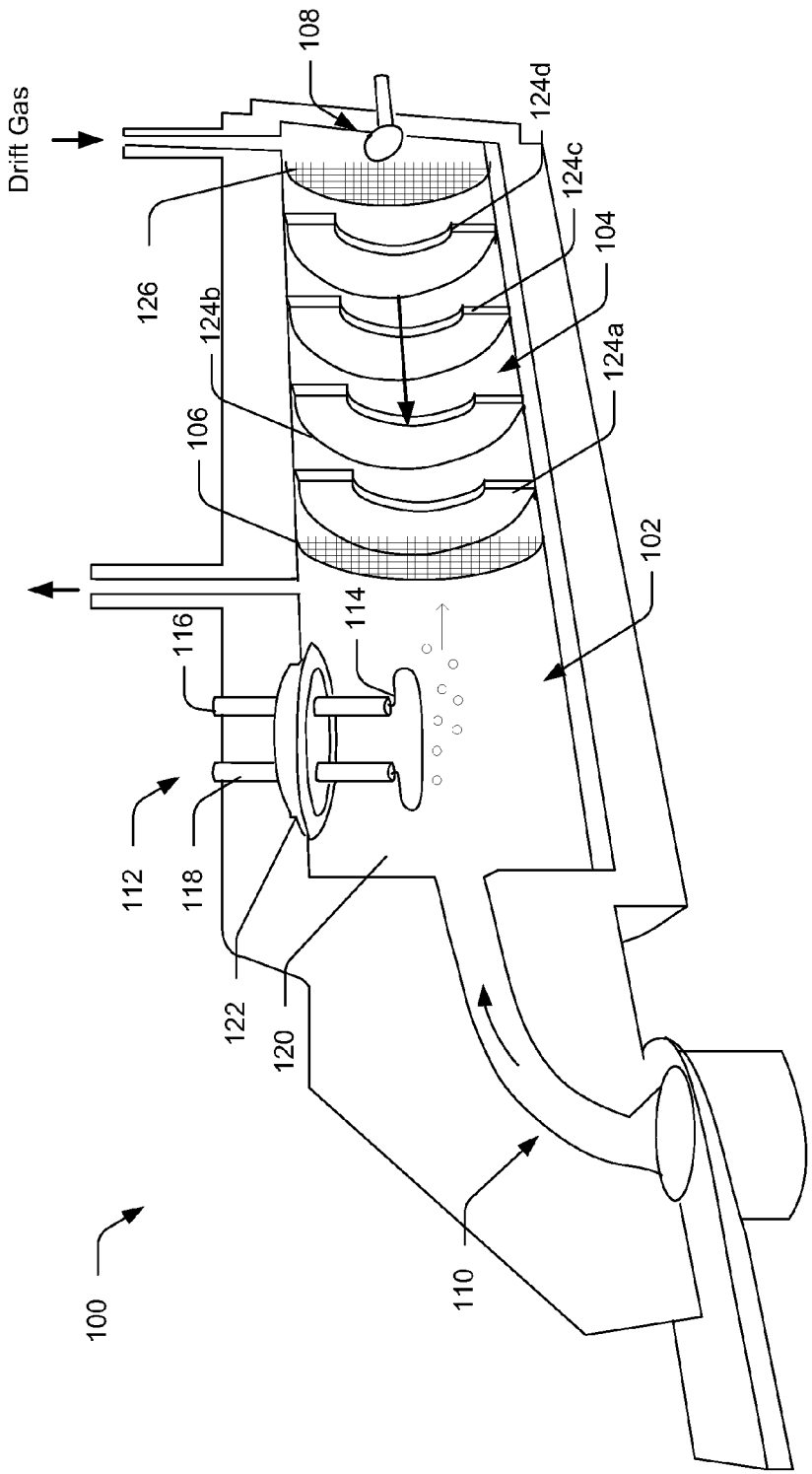
FIG. 1 is an illustration of a spectrometer configured to implement an ionization source that is looped.

FIG. 1 is an illustration of an exemplary spectrometer, such as an ion mobility spectrometer (IMS) 100 that implements electrical ionization of molecules in a sample of interest. The IMS can use direct current (DC) and/or alternating current (AC) electricity. In embodiments, the electrical current can be used to heat the wire. The IMS 100 can identify a large number of molecules, such as explosives and drugs, e.g. narcotics, toxic industrial chemicals, and so forth.

As illustrated, the IMS includes an ionization chamber 102 and a drift chamber 104 that are in fluid communication but are separated by a gate 106 that can control passage of the ions to the drift chamber. A detector 108 can identify the molecules by detecting the ions formed when the ionization source is discharged in the presence of the molecules.

The IMS 100 as illustrated includes an inlet structure 110 that can introduce the molecules to the ionization chamber 102. The inlet structure 110, for example, can use a fluid, such as flow of air (an airflow) to draw the molecules into the ionization chamber 102. Any suitable approach for drawing the sample into the ionization chamber 102 can be used. Example approaches include, but are not limited to fans, pressurized gas systems, a vacuum created by flowing a drift gas through the drift chamber, and the like. A variety of other fluids can be used to draw the sample into the ionization chamber. While an airflow can be used, the IMS 100 substantially operates at ambient pressure.

The IMS 100 can include other structures, such as a desorber, heaters, and/or preconcentrators to aid introduction of the molecules to the ionization chamber 102. For instance, a desorber can be used to vaporize the molecules and/or cause the molecules to enter their gas phase.

As illustrated, the ionization source 112 includes a wire 114 that can generate a corona adjacent to the wire to ionize the molecules. The ionization source can generate the corona when a sufficiently high voltage is applied to the wire 114. In embodiments, a corona is generated when seed ions are present adjacent the wire 114. Seed ions can form based on the thermionic effect or result from photo ionization. The wire 114 can be looped between electrical contacts, such as two posts (respectively, 116,118) that are electrically conductive, although the wire 114 can also be in the form of a coiled filament. The posts 116, 118 may be crimped on the wire or the wire may be otherwise mechanically secured to the posts. In embodiments, the posts 116, 118 are formed of stainless steel or other suitable conductive material. Although the posts can be formed of any conductive material.

The ionization source 112, in the illustrated embodiment, is electrically isolated from the ionization chamber 102, so an electrical potential exists between a wall 120 or walls forming the ionization chamber 102 and the ionization source 112. As a result, the wall 120 can draw the ions away from the ionization source 112 to ionize molecules from the sample and/or or to be drawn towards the gate 106 and drift chamber 104.

An insulator 122, such as a ceramic or glass tube that holds the posts 116, 118, can secure the ionization source 112 in the ionization chamber 102 and electrically insulate the ionization source 112 from the walls 120 forming the ionization chamber. Although the electrical potential between the ionization source 112 and the wall 120 may vary based on implementation conditions, an electrical field that is sufficiently strong adjacent the wire can be used to generate ions, e.g., reactant ions, that can be used to ionize the molecule of interest.

In embodiments, the wire 114 strikes a corona, e.g., a plasma of ions, when the the voltage applied between the wire and ionization chamber walls produces sufficiently strong field near the wire. The temperature of the wire 114 and the electrical potential (e.g., voltage difference) between the wall 120 and the ionization source can influence the plasma. For instance, the ionization source 112 may apply a voltage in the range of approximately 4,000-5,000 volts when the wire is cold, e.g., below 1,000° C. (such as from ambient temperature to 500° C. for a 25 μm diameter wire). These conditions can be applicable for direct current or alternating current ionization sources.

The ionization source 112 can ionize the molecule in multiple steps. The ionization source 112 can generate ions of gases in the ionization chamber that subsequently ionize a molecule of interest. Example gases include nitrogen, water vapor, other gases included in air and other gases in the ionization chamber 102.

The wire's physical properties can influence the corona and ionization of the molecules of interest. The wire's length, diameter cross-section, shape of the loop and/or surface area of the ionization source can influence the corona.

For example, a wire with a larger surface area can form more ions than a smaller diameter wire of similar length. In addition, larger surface area may be associated with lower localized plasma density in comparison to that of a needle-type ionization source. A lower plasma density can lead to increased ionization in comparison to a higher plasma density ionization source, e.g., a needle-type ionization source.

In embodiments, the wire is in the range of one to ten millimeters long (1-10 mm) and/or twenty to eighty micrometers (20-80 μm) in diameter. For example, the source includes a wire with a diameter in the range of approximately 20-30 μm. In embodiments a wire with a diameter of approximately 25 μm is included in the source. The length of the wire and its diameter can be related, for example, a source including a comparatively larger diameter wire may have a shorter length than a smaller diameter wire. These ranges are suitable for desktop type IMS devices base on expected ionization chamber size and IMS operating configurations. In embodiments in which the wire is formed as a coil, the wire can extend up to 100 mm.

The wire's shape also can influence the corona. As illustrated, the wire is an oval in shape. In other embodiments, the wire is formed in other shapes. Example shapes include, but are not limited to, wire that is straight (e.g., a straight loop), rounded loops, coiled and shapes having points or vertices.

In embodiments, wires of different length, diameter, material, surface area, and so on are used based on the corona to be generated and design preferences. A thinner wire can be used to minimize the IMS's overall electrical consumption. Further, a thinner wire can reach a temperature at which the corona strikes with less power consumption than a larger diameter wire. For example, an IMS uses less electricity to cause a 20 μm wire to strike a corona in comparison to a 50 μm diameter wire of similar length and material.

In embodiments, a larger diameter wire is implemented to increase the number of ions formed, the life expectancy of the source, and so forth in comparison to smaller diameter wire of similar length and material. A larger diameter wire in the range of approximately 50 μm may have a longer operational period between cleaning cycles, withstand a greater number of cleaning cycles and so forth relative to a smaller diameter wire of the same length and material. A larger diameter wire has more surface area to form the corona and may experience less overall fouling in comparison to a comparable thinner wire. This may permit the IMS to perform more runs in between high temperature cleaning cycles used to remove contaminates from the ionization source 112.

As illustrated, the wire 114 is composed of a single strand. In embodiments, the wire 114 is composed of multiple strands. The individual strands formed of the same (or substantially the same) material or of different materials based on design preference. Strands of different material can be used to tailor the corona's properties.

The wire's chemical/material properties can influence the corona. In embodiments, the material or materials forming the wire are selected for their: electrical conductance, electrical resistance, ability to maintain high temperature (e.g., approximately 1000° C. or above). For example, the wire 114 operates in the range of 500° C. to 1,500° C. depending on implementation conditions. In other examples, the wire operates from approximate 800° C. to 1,200° C. The operating range, voltage to be applied and other operating parameters can be varied based on, but not limited to, an expected sample identity, power consumption, the material forming the wire, the ionization chamber's size, In implementations, the wire's operating temperature is associated with a property of the material forming the wire, e.g., the wire operates in the material's orange hot region from about the material's slightly orange hot color to approximately its red hot color. In embodiments, a temperature associated with the material's a slightly orange hot color may be selected to minimize overall power consumption. Other properties that can be considered include, but are not limited to, the material's melting point, a type of molecule expected or electrical current frequency. Additional properties impacting the wire's material selection include resistance to: oxidation, fouling, material erosion and so forth. A Platinum-rhodium alloy is selected, for example, for its high melting point and resistance to oxidation.

Suitable wire materials include, for example, platinum, rhodium, iridium, nichrome, tungsten, tantalum, iron-chromium-aluminum alloys (such as KANTHAL, Sandvik Heating Technology, Hallstahammar Sweden), combinations thereof (including alloys), and the like materials. For example, a looped platinum wire having a 50 μm diameter strikes a corona at an orange hot temperature (e.g., approximately 1000° C.) when a 0.7 amp electrical current is applied. In embodiments, a wire, such as a platinum based wire, having 25 μm diameter a may generate a corona at a slightly orange hot temperature at 0.35 amps.

The ionization source 112 may use a comparatively higher voltage when the relative humidity of the ionization chamber 102 is in the range of one to three percent. For example, a voltage of above 1,000 volts can be used when the relative humidity of the ionization chamber 102 is in the range of one to three percent. The ionization source 112 can implement a lower voltage when the relative humidity of the ionization chamber 102 is in the parts per million range, such as when the IMS uses a drying agent in a re-circulating system. In an example, a voltage of below 1,000 volts is used when the humidity is in the parts per million range.

While the wire 114 is to be sufficiently hot to strike the corona during operation, overheating the wire beyond this temperature may degrade the wire and shorten its useful life. In contrast, if the temperature of the wire is too low, the corona may pulse instead of remaining substantially consistent, although a cold wire corona can be stabilized by electronic means. Operation of the IMS 100 can be configured to avoid these issues.

In use, the wire's temperature and electrical charge may not be uniform along its length. For example, the temperature of the wire 114 may be hotter adjacent the wire's midpoint (e.g., in the middle of the loop) in comparison to the ends adjacent to the posts. In this example, the wire 114 forms the corona adjacent to the middle of the wire's loop.

The suitability of the above ranges relates to a variety of factors, such as the IMS's electrical power consumption, the expected life of the wire, temperature at which the corona is to strike, an expected amount of sample, what material the wire is made of, and so on.

Although the ionization source 112 can form a variety of ions with different mass to charge ratios, an ion comprising the molecule with a single positive or negative charge may be of interest in identifying the molecule. For example, the detector 108 included in the drift chamber 104 can differentiate between ions based on that ion's ion mobility that is related to one or more of the ion's mass, geometry, and its charge.

The IMS's operational and physical configurations can influence operation of the ionization source 112. For example, the ionization source's physical and/or chemical properties (e.g., the looped wire's properties), as well as, the voltage, current and frequency applied to the current are related to a variety of IMS properties. Example properties include, but are not limited to, one or more of: ionization chamber's size, the ionization source's current, a predicted airflow rate or a drift gas flow rate. Other properties include, an expected amount of sample to be ionized, a voltage difference between the ionization source and the walls forming the ionization chamber or ionization source/corona temperature during ionization.

The magnitude of the ionization source's voltage may be adjusted depending on drift gas, pressure, wire temperature and/or wire diameter. A lower voltage can be used when a noble gas is used as the drift gas, while a higher voltage is used for air and air containing water vapor. A lower voltage can be used with reduced ambient pressure. For example, a higher voltage is used at sea level in comparison to operating an IMS at a higher elevation.

The IMS 100 can pulse an electrical current to the ionization source 112 periodically, based on when a sample is introduced into an inlet port, when the gate allows ions into the drift chamber, upon the occurrence of an event, and so on. In embodiments, the ionization source has a positive charge (positive mode), a negative charge (negative mode) or can switch between positive and negative modes in accordance with the IMS electric field polarity. The ionization source and/or the wall 120 can switch between positive and negative modes at approximately twenty (20) milliseconds, ten (10) milliseconds, or less intervals—although a variety of timing scenarios are contemplated.

The gate 106 is configured to control passage of ions from the ionization chamber to the drift chamber 104. The gate can be, for example, a Bradbury Nielson gate that comprises a mesh of wires through which the IMS applies an electrical charge. For instance, a controller, under computer control, can pass a charge to the gate 106 to control when and what ions can enter the drift chamber 104. The gate 106 controls entry of the ions through application of a repulsing charge on the gate 106. The gate 106 allows ions to pass to the drift chamber 104 when the repelling charge is dropped.

The opening and/or closing of the gate 106 can be timed based on when the corona is struck or some period thereafter. For example, the gate 106 is opened to allow a range of ions to enter the drift chamber 104 before an electrical charge is applied to the gate 106 to prevent ions from entering the drift chamber 104.

A series of electrodes 124a-d, e.g., focusing rings and/or a guard grid 126 are included in the drift chamber 104 to focus and/or direct the ions toward the detector 108, e.g. a charged plate. In embodiments, the electrodes 124a-d are ring shaped and disposed along the length of the drift chamber 104.

The IMS 100 can include a variety of components to aid/promote identification of the molecule of interest. For example, the IMS 100 includes one or more cells configured to contain calibrant and/or dopant. Dopant is used to form an ion with the molecule that is more easily identified than the molecule alone.

In embodiments, the IMS 100 operates under computer control. For example, a processor is included with or in the IMS to control the IMS's components and functions described herein using software, firmware, hardware (e.g., fixed logic circuitry), manual processing, or a combination thereof. The terms "functionality," "service," and "logic" as used herein generally represent software, firmware, hardware, or a combination of software, firmware, or hardware in conjunction with controlling the IMS 100. In the case of a software implementation, the module, functionality, or logic represents program code that performs specified tasks when executed on a processor (e.g., CPU or CPUs). The program code may be stored in one or more computer-readable memory devices (e.g., memory and/or one or more tangible media), and so on. The structures, functions, approaches, and techniques described in this document can be implemented on a variety of commercial computing platforms having a variety of processors.

Processors are not limited by the materials from which they are formed or the processing mechanisms employed therein. For example, the processor may be comprised of semiconductor(s) and/or transistors (e.g., electronic integrated circuits (ICs)).

Memory can be included with the processor. The memory 106 can store data, such as a program of instructions for operating the IMS, data, and so on. Although a single memory device can be used, a wide variety of types and combinations of memory (e.g., tangible memory) may be employed, such as random access memory (RAM), hard disk memory, removable medium memory, external memory, and other types of computer-readable storage media.

In additional embodiments, a variety of analytical devices may make use of the structures, techniques, approaches, and so on described herein. Thus, although an IMS device is described throughout this document, a variety of analytical instruments may make use of the described techniques, approaches, structures, and so on. These devices may be configured with limited functionality (e.g., thin devices) or with robust functionality (e.g., thick devices). Thus, a device's functionality may relate to the device's software or hardware resources, e.g., processing power, memory (e.g., data storage capability), analytical ability, and so on. For example, the corona source can also be used in other types of spectrometry involving an ionization process such as mass spectrometers (MS).

Moreover, the processor controlling the IMS 100 may be configured to communicate with a variety of different networks. For example, the networks may include the Internet, a cellular telephone network, a local area network (LAN), a wide area network (WAN), a wireless network, a public telephone network, an intranet, and so on.

Figure 2:
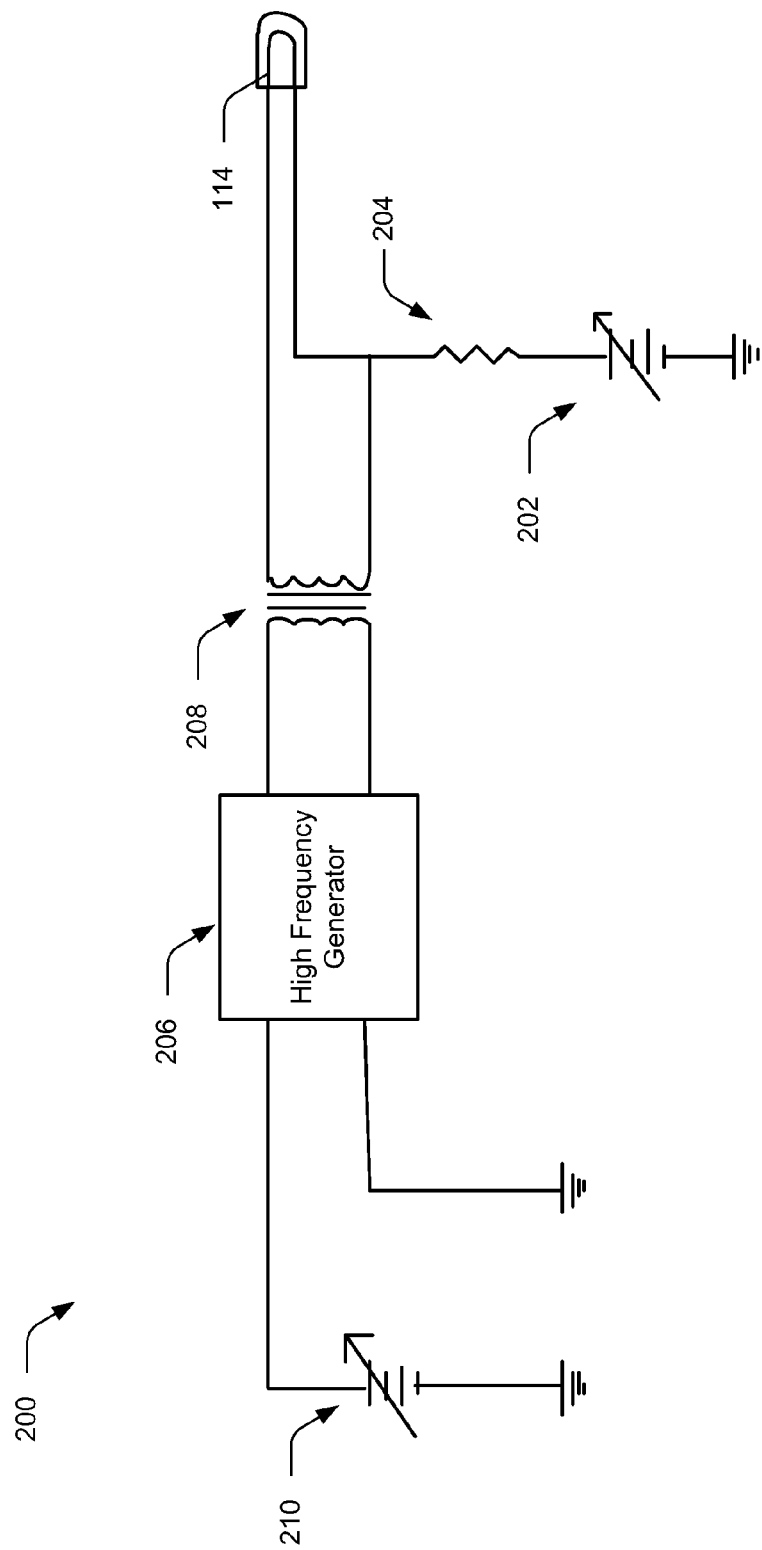
FIG. 2 is a schematic illustration of an electrical system in accordance with an embodiment of this disclosure.

FIG. 2 is a schematic illustration of an electrical system 200 that is used in embodiments consistent with this disclosure. Although an AC electrical system 200 is illustrated, a DC electrical system can be implemented. When a DC system is intended, a rectifier can be included in the system 200.

As illustrated, the wire 114, that is looped, is electrically coupled to a high voltage source 202. A resistor 204 is included between the high voltage source 202 and the wire 114. The resistor 204 limits the current flowing to the wire 114 to protect it.

A high frequency generator 206 is included to oscillate the frequency of the current flowing through the wire 114. For example, the high frequency generator 206 may vary the frequency of the current passing through the wire 114 between ten kilohertz (10 kHz) to 3 megahertz (3 MHz), although other frequencies are contemplated. In embodiments, an AC's frequency is selected based on various design considerations such as transformer structure. The amount of heat applied to the wire depends on the current flowing through it relative to its resistance and diameter. The primary side of the isolation transformer 208 is driven by a high frequency generator 206 supplied by a low voltage power source 210, whereas the high current secondary side of the isolation transformer 208 is also connected to a high voltage power supply.

Figure 3:
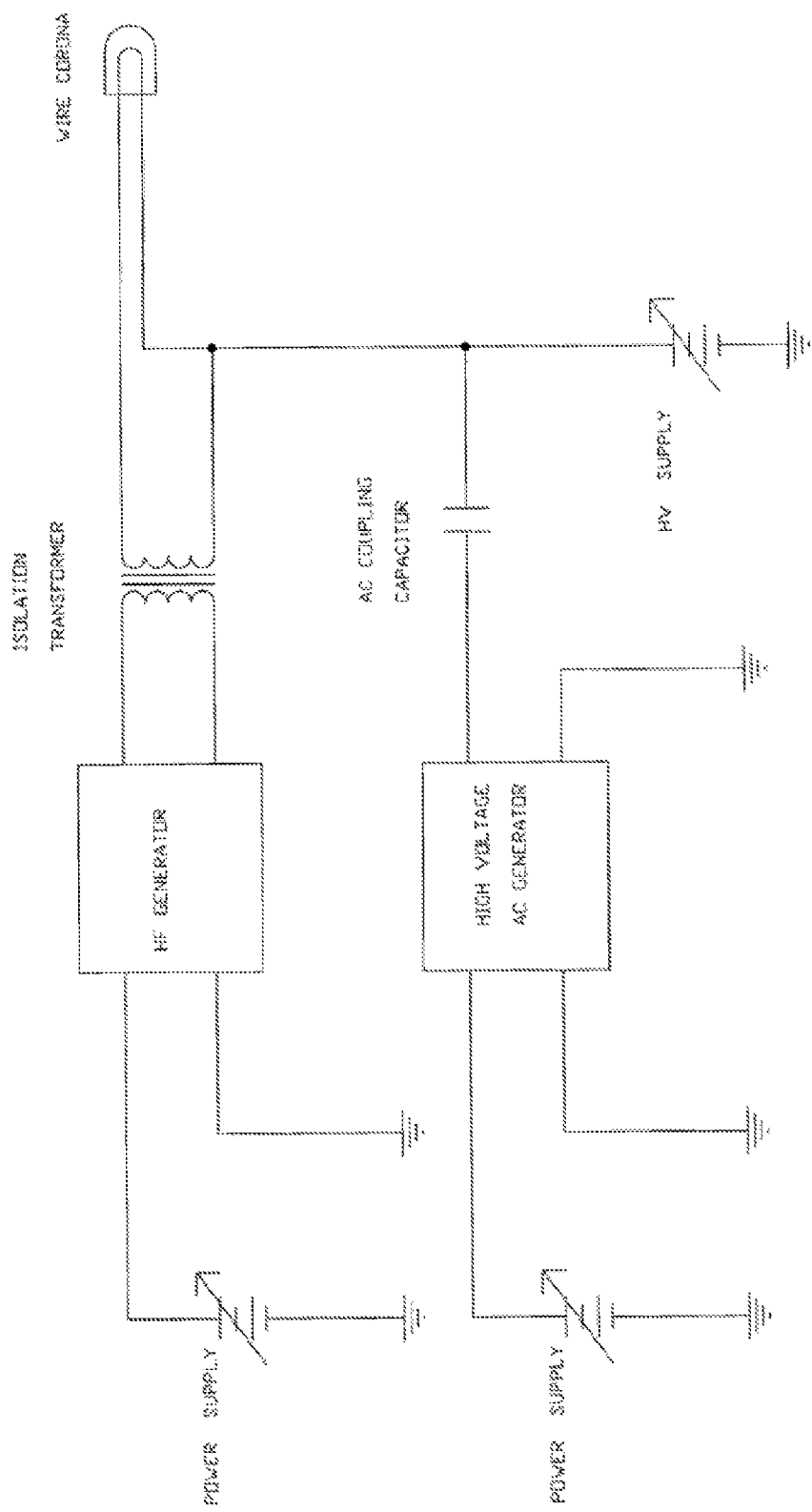
FIG. 3 is a schematic illustration of secondary side of an isolation transformer in accordance with this disclosure.

FIG. 3 is a general illustration of a circuit in which a secondary side of an isolation transformer, such as isolation transformer 208, has both DC and AC high voltage supplies coupled to it to provide control over the operation of a source. In this embodiment, the high frequency current controls the temperature of the wire corona source, the DC high voltage can control the trajectories of the ions within the ionization region, and the AC high voltage provides additional control of the number of ions produced by the wire source.

Figure 4:
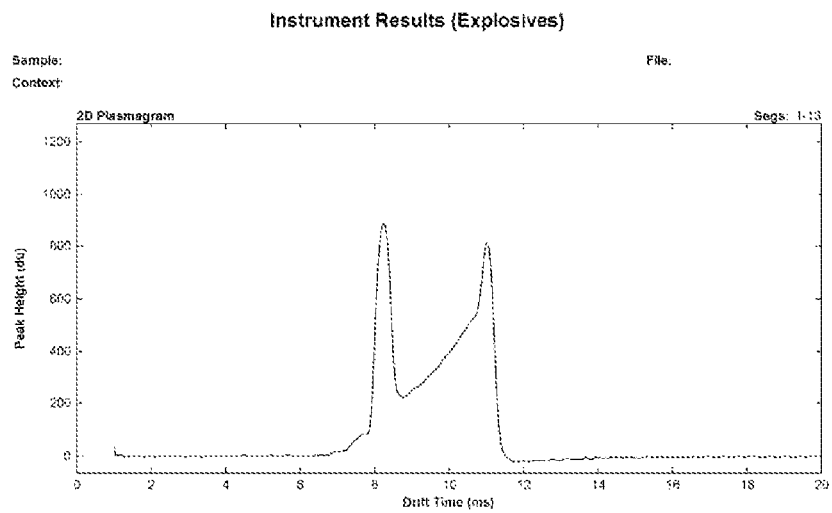
FIG. 4 is an illustration of a sample plasmagram that was obtained from a spectrometer including an ionization source in accordance with this disclosure.

FIG. 4 is an example plasmagram generated from an IMS utilizing a looped ionization source consistent with the present disclosure. While an IMS with a looped ionization source can operate with a similar timing schedule as a needle-type ionization source, the number of ions formed and detected can be greater than needle-type ionization sources.

Figure 5:
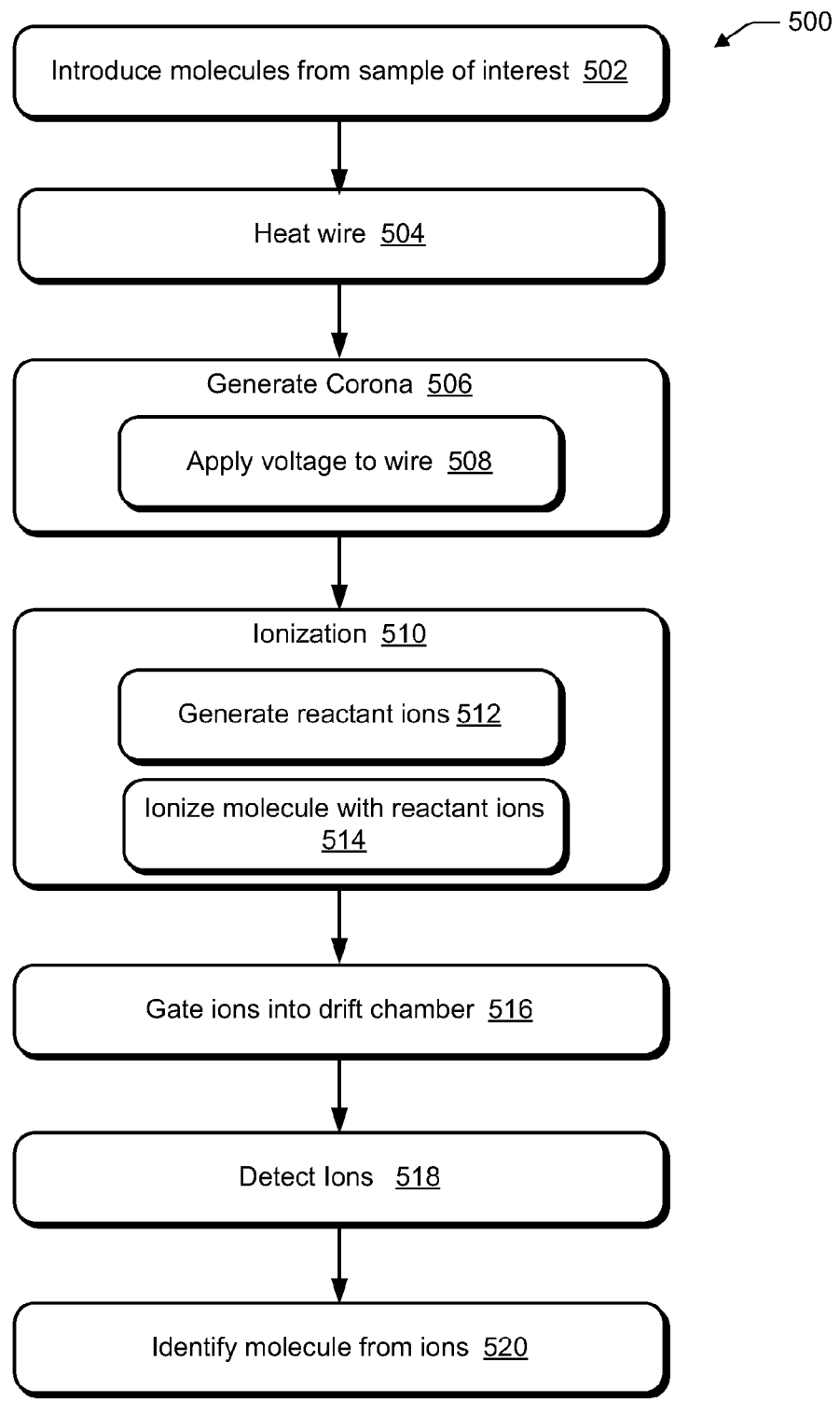
FIG. 5 is a flow diagram depicting a procedure in an example implementation that implements a looped ionization source.

FIG. 5 depicts a procedure 500 in an example implementation that implements a looped ionization source to ionize a molecule or molecules of interest.

Figure 6:
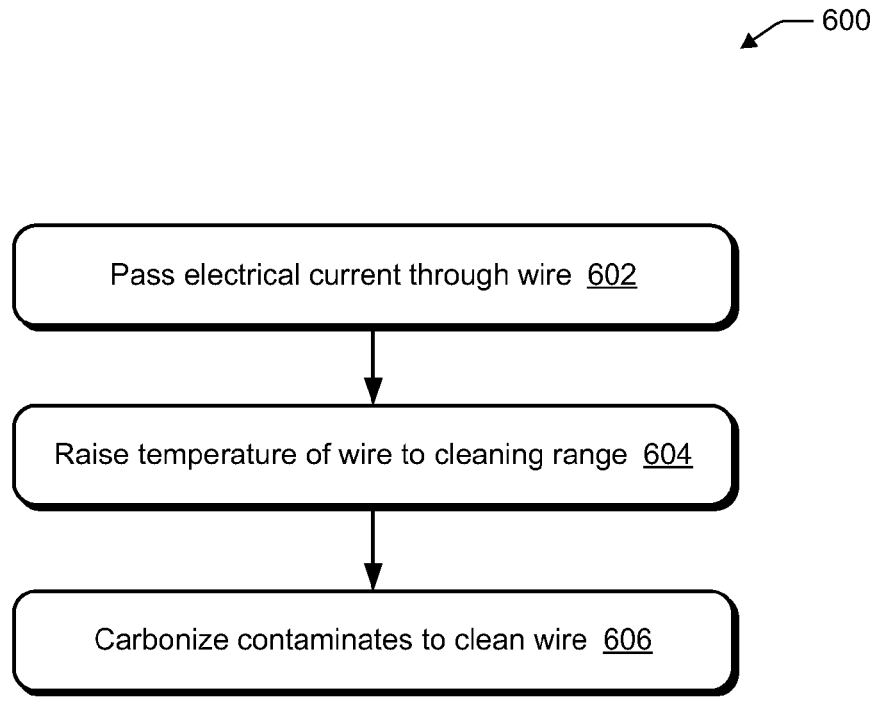
FIG. 6 is a flow diagram depicting a cleaning procedure in an example implementation for a looped ionization source.

FIG. 6 illustrates a cleaning procedure 600 that can eliminate fouling on a looped ion source.

Exemplary Procedures

The following discussion describes procedures that may be implemented utilizing the previously described IMS 100 components, techniques, approaches, and modules. Aspects of each of the procedures may be implemented in hardware, software, or a combination thereof. The procedures are shown as a set of blocks that specify operations performed by one or more devices (e.g., a spectrometer or components) and are not necessarily limited to the orders shown for performing the operations by the respective blocks. In portions of the following discussion, reference will be made to the IMS 100 of FIG. 1 the electrical system 200 of FIG. 2.

FIG. 5 depicts a procedure 500 in an example implementation that implements a looped ionization source to ionize a molecule or molecules of interest. The molecules may be identified by detecting ions that result from ionization of the molecule included in a sample of interest. In embodiments, the procedure 500 is performed under computer control.

Molecules from the sample of interest are introduced to an ionization chamber including a looped ionization source (block 502). The molecules may be collected using a pre-concentrator that collects a sufficient number of molecules to permit detection. During pre-concentration, a pre-concentrator collects molecules for a period of time before releasing them as a group or bolus. In addition, a heater can be used to vaporize or cause the molecules to enter a gas phase to promote ionization.

Additionally, the molecules may pass through a membrane that is configured to limit what material enters the ionization chamber 102. For example, the membrane is used to minimize humidity in the ionization chamber 102 while permitting molecules from the sample of interest to pass.

Optionally, dopant can be introduced in conjunction with the molecules of interest. For example, 2,4-pentanedione is introduced to assist in identifying toxic industrial chemicals and nitrogen compounds. A variety of dopants may be used based on an expected composition of the molecule of interest (e.g., explosives, narcotics and so forth).

Optionally, a looped ionization source is heated (block 504). For example, an alternating current is passed through a wire to heat it to a predetermined operating temperature. For example, a platinum wire can operated at approximately 1000° C., (e.g., when the platinum is orange hot). The temperature and conditions of the wire can depend on a variety of factors and/or conditions, as noted above.

A corona is generated (block 506). The corona can form when a sufficiently high electrical potential is applied an electrical adjacent a looped ionization source reaches a sufficiently high voltage to form a plasma of ions adjacent to the looped ionization source (block 508). A voltage difference of approximately 4,000 volts can generate a corona adjacent a wire when the wire is approximately at ambient temperature. Corona generation can be associated with the existence of seed ions that can be generated via the thermionic effect or result from photo ionization.

Ionization of the molecules of interest (block 510) can occur in a variety of ways. For example, an ionization source can ionize a molecule through various multistep processes using ions that are formed in the plasma.

In embodiments, reactant ions are generated by the corona (block 512). The reactant ions ionize the molecule of interest (block 514). For example, the ionization source forms ions adjacent to the wire 114 that are subsequently drawn away to ionize the molecules of interest. Reactant ions may be ionized gases (e.g., nitrogen and gases in air) and other gases in the ionization chamber, such as water, and so forth. Although fragmentation of the molecule of interest is possible, ionization can be controlled to result in "soft" ionization thereby minimizing fragmentation of the molecule in favor of the molecule carrying a single charge, e.g., a plus one or minus one charge.

The ions from the molecule of interest are gated to control passage of the ions into a drift chamber (block 516). For example, a controller for the gate 106 may temporarily drop the gate's charge to permit ions to enter the drift chamber 106. In embodiments, the gate 106 is used to control when and which ions are permitted to enter the drift chamber. In embodiments, an electrical field, established by electrodes in the drift chamber, draws the ions towards the detector while a drift gas flows in a generally opposite direction.

The ions are detected (block 518) as the ions come in contact with, for example, the detector 108. For example, the IMS 100 times how long it takes an ion to reach the detector 108 after the gate 106 is opened. This time-of-flight can be associated with the underlying molecule.

The ion's ion mobility is used to identify the molecule associated with the ion (block 520). For example, a computer can be used to compare the detector's output with a library of plasmagrams of known ions.

Once one or multiple runs are complete, an ionization source may become fouled. For example, an IMS with a cold ionization source, e.g., a source that is not appreciably heated may become fouled with combustion residues. Residue, such as organic deposits from the sample of interest and other materials in the ionization chamber, can foul the ionization source's surface. The ionization source may perform poorly once there is sufficient buildup on its surface.

FIG. 6 illustrates a cleaning procedure 600 that can eliminate fouling on a looped ion source. For example, the method 600 is used to clean an ionization source that operates at ambient conditions, e.g., is not appreciably heated during operation. The cleaning procedure 600 can be used to eliminate organic deposits and other surface contamination on, for example, the wire's surface. An IMS can initiate this cleaning procedure 600 periodically (at a time interval) and/or upon an occurrence of an event, such as when poor performance is detected, more electrical current is used to raise the ionization source's temperature and so on.

An electrical current is passed through the looped wire (block 602). In embodiments, the ionization source passes a greater electrical current through the wire, in comparison to standard operation, while the voltage is substantially similar to that used in during normal operation. The current may be ramped up to minimize potential damage to the wire caused by thermal stress, ensure even heating along the wire and so forth.

The wire's temperature is raised to a cleaning range (block 604). For example, the ionization source 112 may raise the wire temperature to above its normal operating temperature of between 500° C.-1,500° C. In embodiments, the wire's temperature is raised above 1500° C. while staying safely below the wires melting point to avoid damage, e.g., 1768° C. for platinum. A smaller diameter wire can further be heated and cooled within short periods of time, usually in less then a second, which in turn allows for a brief cleaning procedure of less than a few seconds.

Contaminates are carbonized from the wire (block 606). The temperature of the wire can be maintained at a cleaning temperature for a predetermined period of time or until the occurrence of an event. For example, cleaning can stop when a drop occurs in an amount of current that is used to raise the wire's temperature. This can indicate surface contaminates have been carbonized from the wire.

Subsequently, the wire may be permitted to cool to its operating temperature or ambient temperature. The IMS, subsequently, may actively or passively cool the source to its operating temperature or ambient temperature.

Although the invention has been described in language specific to structural features and/or methodological acts, it is to be understood that the invention defined in the appended claims is not necessarily limited to the specific features or acts described. Rather, the specific features and acts are disclosed as example forms of implementing the claimed invention.

We claim:

1. A spectrometer comprising:
   a) a wall, that is capable of conducting electricity, that forms an ionization chamber; and
   b) an ionization source, disposed in the ionization chamber, wherein the ionization source comprises a wire looped between two electrical contacts, and the electrical contacts are configured to pass a current through the wire, wherein said current heats the wire, and wherein a corona is formed when a voltage is applied between the ionization source and the ionization chamber.

2. The spectrometer of claim 1, wherein the spectrometer comprises an ion mobility spectrometer configured to operate substantially at ambient pressure.

3. The spectrometer of claim 2, wherein the ionization source wire is configured to strike a corona substantially adjacent to its midpoint.

4. The spectrometer of claim 2, wherein the ionization source is configured to strike a corona in the range of 500° C. to 1,500° C.

5. The spectrometer of claim 2, wherein the ionization source comprises a wire formed of at least one of: platinum; rhodium; nichrome; iridium; tungsten; tantalum; a platinum-rhodium alloy; a platinum-rhodium-irridium alloy; a platinum-irridium alloy; or an iron-chromium-aluminum alloy.

6. The spectrometer of claim 1, wherein the current comprises an alternating electrical current or a direct electrical current.

7. The spectrometer of claim 1, wherein the ionization source comprises a coiled wire.

8. The spectrometer of claim 1, wherein the wire is electrically conductive and electrically insulated from the wall of an ionization chamber.

9. The ion mobility spectrometer of claim 1, wherein the electrical contacts are configured to pass an alternating electrical current through the wire.

10. The ion mobility spectrometer of claim 1, wherein diameter of the wire is between twenty and eighty micrometers (20-80 µm).

11. The ion mobility spectrometer of claim 1, wherein the looped wire is coiled or rounded along its length.

12. The ion mobility spectrometer of claim 1, wherein the ionization chamber is substantially at ambient pressure.

13. The ion mobility spectrometer of claim 8, wherein the looped wire is formed of at least one of: platinum; rhodium; nichrome; iridium; tungsten; tantalum; a platinum-rhodium alloy; a platinum-rhodium-irridium alloy; a platinum-irridium alloy; or an iron-chromium-aluminum alloy.

14. The ion mobility spectrometer of claim 1, wherein the ion mobility spectrometer is configured to apply an electrical current of approximately 0.7 amps to the ionization source.

15. The ion mobility spectrometer of claim 1, wherein heating the wire improves quality of ionization.

16. The ion mobility spectrometer of claim 15, wherein heating the wire reduces the voltage required to form the corona.

17. The spectrometer of claim 4, wherein the ionization source is configured to strike a corona in the range of 800° C. to 1,200°C.

18. The spectrometer of claim 17, wherein the ionization source is configured to strike a corona at approximately 1000° C.

* * * * *